United States Patent
Shute et al.

(10) Patent No.: US 12,138,464 B2
(45) Date of Patent: Nov. 12, 2024

(54) LONG TERM PATIENT DEVICE DATA INTEGRITY TRACKING SYSTEM AND METHODS

(71) Applicant: Cardiac Pacemakers, Inc., St. Paul, MN (US)

(72) Inventors: Jonathan Bennett Shute, Eagan, MN (US); Kevin G. Wika, Blaine, MN (US); Michael Sheehan Seeberger, Afton, MN (US); James F. Hiebert, Delano, MN (US); Andrew Bomett, Inver Grove Heights, MN (US); Michael Marxhausen, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 503 days.

(21) Appl. No.: 17/480,702

(22) Filed: Sep. 21, 2021

(65) Prior Publication Data
US 2022/0088399 A1 Mar. 24, 2022

Related U.S. Application Data

(60) Provisional application No. 63/082,180, filed on Sep. 23, 2020.

(51) Int. Cl.
*A61N 1/372* (2006.01)
*G16H 10/60* (2018.01)
(Continued)

(52) U.S. Cl.
CPC ......... *A61N 1/37282* (2013.01); *G16H 10/60* (2018.01); *G16H 40/67* (2018.01); *H04L 9/3236* (2013.01); *H04L 63/123* (2013.01)

(58) Field of Classification Search
CPC ............ A61N 1/37254; A61N 1/37282; A61N 1/37211
See application file for complete search history.

(56) References Cited

U.S. PATENT DOCUMENTS

| | | | |
|---|---|---|---|
| 10,673,617 | B1 | 6/2020 | Antoniou et al. |
| 2005/0203582 | A1 | 9/2005 | Healy et al. |

(Continued)

FOREIGN PATENT DOCUMENTS

| | | |
|---|---|---|
| KR | 20020064292 | 8/2002 |
| WO | 2019210092 | 10/2019 |

OTHER PUBLICATIONS

Liang, Xueping, et al. "Integrating Blockchain for Data Sharing and Collaboration in Mobile Healthcare Applications," Conference Paper, 2017, IEEE (6 pages).

(Continued)

*Primary Examiner* — George R Evanisko
(74) *Attorney, Agent, or Firm* — Pauly, DeVries Smith & Deffner LLC

(57) ABSTRACT

Embodiments herein relate to systems for tracking and maintaining the integrity of patient device data over extended periods of time. In a first aspect, a medical device system is included having an implantable device that can include a control circuit, a communication circuit, and one or more sensors. The system can also include an external device including a control circuit and a communication circuit. The external device can be configured to receive patient data from the implantable device and execute a hashing operation on units of received patient device data and one or more previous digest packets to create new digest packets. The external device can be configured to store the new digest packets and forward digest packets onto another device of the medical device system when requested to (Continued)

allow patient data to be authenticated. Other embodiments are also included herein.

13 Claims, 11 Drawing Sheets

(51) Int. Cl.
*G16H 40/67* (2018.01)
*H04L 9/32* (2006.01)
*H04L 9/40* (2022.01)

(56) References Cited

U.S. PATENT DOCUMENTS

| | | |
|---|---|---|
| 2019/0371457 A1 | 12/2019 | Paffel et al. |
| 2021/0058257 A1* | 2/2021 | Pepin ................. A61N 1/36142 |

OTHER PUBLICATIONS

"International Preliminary Report on Patentability," for PCT Application No. PCT/US2021/05126 mailed Apr. 6, 2023 (8 pages).
"International Search Report and Written Opinion," for PCT Application No. PCT/US2021/051269 mailed Dec. 6, 2021 (14 pages).
Siddiqi, Muhammad, et al. "Secure Opportunistic Contextual Logging for Wearable Healthcare Sensing Devices," IEEE Transactions on Dependable and Secure Computing, vol. 16, No. 2, Mar./Apr. 2021 (12 pages).
"Response to Communication Pursuant to Rules 161(1) and 162 EPC," for European Patent Application No. 21790034.9 filed Nov. 8, 2023 (4 pages).

* cited by examiner

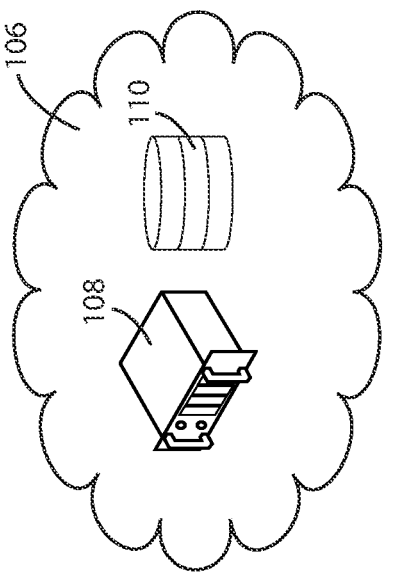
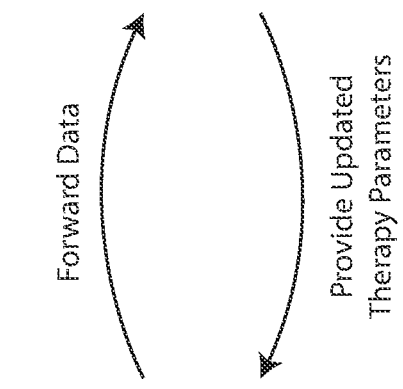
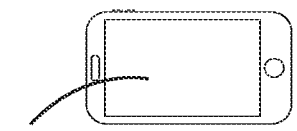
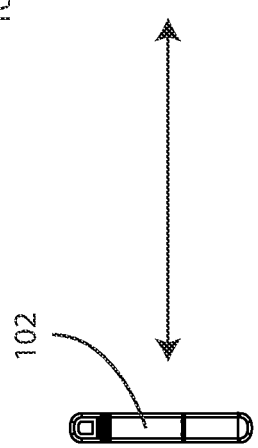
FIG. 7

LONG TERM PATIENT DEVICE DATA INTEGRITY TRACKING SYSTEM AND METHODS

This application claims the benefit of U.S. Provisional Application No. 63/082,180, filed Sep. 23, 2020, the content of which is herein incorporated by reference in its entirety.

FIELD

Embodiments herein relate to systems for tracking and maintaining the integrity of patient device data over extended periods of time.

BACKGROUND

Medical devices are producing increasing amounts of data. As one example, implantable devices are increasing being fitted with sensors that can gather substantial amounts of data related to the patient's health as well as related to the status of the device itself. Such data can be useful for various purposes including monitoring the health status of the patient, influencing physician's decisions, providing feedback for improvements to devices, and providing information for regulatory bodies, amongst other uses.

SUMMARY

Embodiments herein relate to systems for tracking and maintaining the integrity of patient device data over extended periods of time. In a first aspect, a medical device system is included having an implantable device that can include a control circuit, a communication circuit, and one or more sensors. The system can also include an external device including a control circuit and a communication circuit. The external device can be configured to receive patient data from the implantable device and execute a hashing operation on units of received patient device data and one or more previous digest packets to create new digest packets. The external device can be configured to store the new digest packets and forward digest packets onto another device of the medical device system when requested to allow patient data to be authenticated.

In a second aspect, in addition to one or more of the preceding or following aspects, or in the alternative to some aspects, the medical device system further can include a remote server and a remote database, wherein the remote server serves as another device of the medical device system.

In a third aspect, in addition to one or more of the preceding or following aspects, or in the alternative to some aspects, the implantable device is configured to execute a hashing operation on units of patient data and one or more previous digest packets to create new digest packets.

In a fourth aspect, in addition to one or more of the preceding or following aspects, or in the alternative to some aspects, the implantable device is configured to forward digest packets onto the external device.

In a fifth aspect, in addition to one or more of the preceding or following aspects, or in the alternative to some aspects, the external device is configured to compare digest packets generated with the implantable device against digest packets generated by the external device.

In a sixth aspect, in addition to one or more of the preceding or following aspects, or in the alternative to some aspects, the remote server is configured to store both patient data and digest packets in the remote database.

In a seventh aspect, in addition to one or more of the preceding or following aspects, or in the alternative to some aspects, the remote server is configured to periodically rehash patient data and previous digest packets and compare the resulting new digest packets against previously received digest packets nominally representing the same patient data and previous digest packets.

In an eighth aspect, in addition to one or more of the preceding or following aspects, or in the alternative to some aspects, the remote server is configured to roll back to earlier patient data and earlier digest packets when a comparison of digest packets reveals a difference.

In a ninth aspect, in addition to one or more of the preceding or following aspects, or in the alternative to some aspects, the remote server is configured to digitally sign new digest packets when a comparison of digest packets reveals no differences.

In a tenth aspect, in addition to one or more of the preceding or following aspects, or in the alternative to some aspects, the remote server is configured to send a request to a plurality of implantable devices requesting them to transmit their identity and their most recent digest packets.

In an eleventh aspect, in addition to one or more of the preceding or following aspects, or in the alternative to some aspects, the remote server is configured to execute a hashing operation on units of received patient device data and one or more previous digest packets as received from a group of external devices, and separately execute a hashing operation on units of received patient device data and one or more previous digest packets as received from a subset of the group of external devices.

In a twelfth aspect, in addition to one or more of the preceding or following aspects, or in the alternative to some aspects, a subset of the group of external devices represents external devices from a particular site in a clinical study.

In a thirteenth aspect, in addition to one or more of the preceding or following aspects, or in the alternative to some aspects, the external device executes the hashing operation in response to a detected event.

In a fourteenth aspect, a medical device system is included having an implantable device that can include a control circuit, a communication circuit, and one or more sensors, wherein the implantable device is configured to execute a hashing operation on units of patient data and one or more previous digest packets to create new digest packets. The implantable device can also be configured to forward at least one of patient data and new digest packets onto another device.

In a fifteenth aspect, in addition to one or more of the preceding or following aspects, or in the alternative to some aspects, the implantable device is further configured to receive patient data from external devices.

In a sixteenth aspect, in addition to one or more of the preceding or following aspects, or in the alternative to some aspects, the implantable device is configured to discard units of patient data and digest packets, but is configured to discard units of patient data following a different schedule than for discarding digest packets.

In a seventeenth aspect, in addition to one or more of the preceding or following aspects, or in the alternative to some aspects, the implantable device is configured to forward only patient data and not new digest packets onto an external device.

In an eighteenth aspect, in addition to one or more of the preceding or following aspects, or in the alternative to some aspects, further can include a remote server, wherein the implantable device is configured to forward digest packets onto the remote server when requested to allow patient data to be authenticated.

In a nineteenth aspect, in addition to one or more of the preceding or following aspects, or in the alternative to some aspects, the remote server is configured to periodically rehash patient data and previous digest packets and compare the resulting new digest packets against previously received digest packets nominally representing the same patient data and previous digest packets.

In a twentieth aspect, in addition to one or more of the preceding or following aspects, or in the alternative to some aspects, the remote server is configured to roll back to earlier patient data and earlier digest packets when a comparison of digest packets reveals a difference and digitally sign the resulting new digest packets when the comparison reveals no differences.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 7 is a schematic view of components of a system in accordance with various embodiments herein.

DETAILED DESCRIPTION

Figure 1:
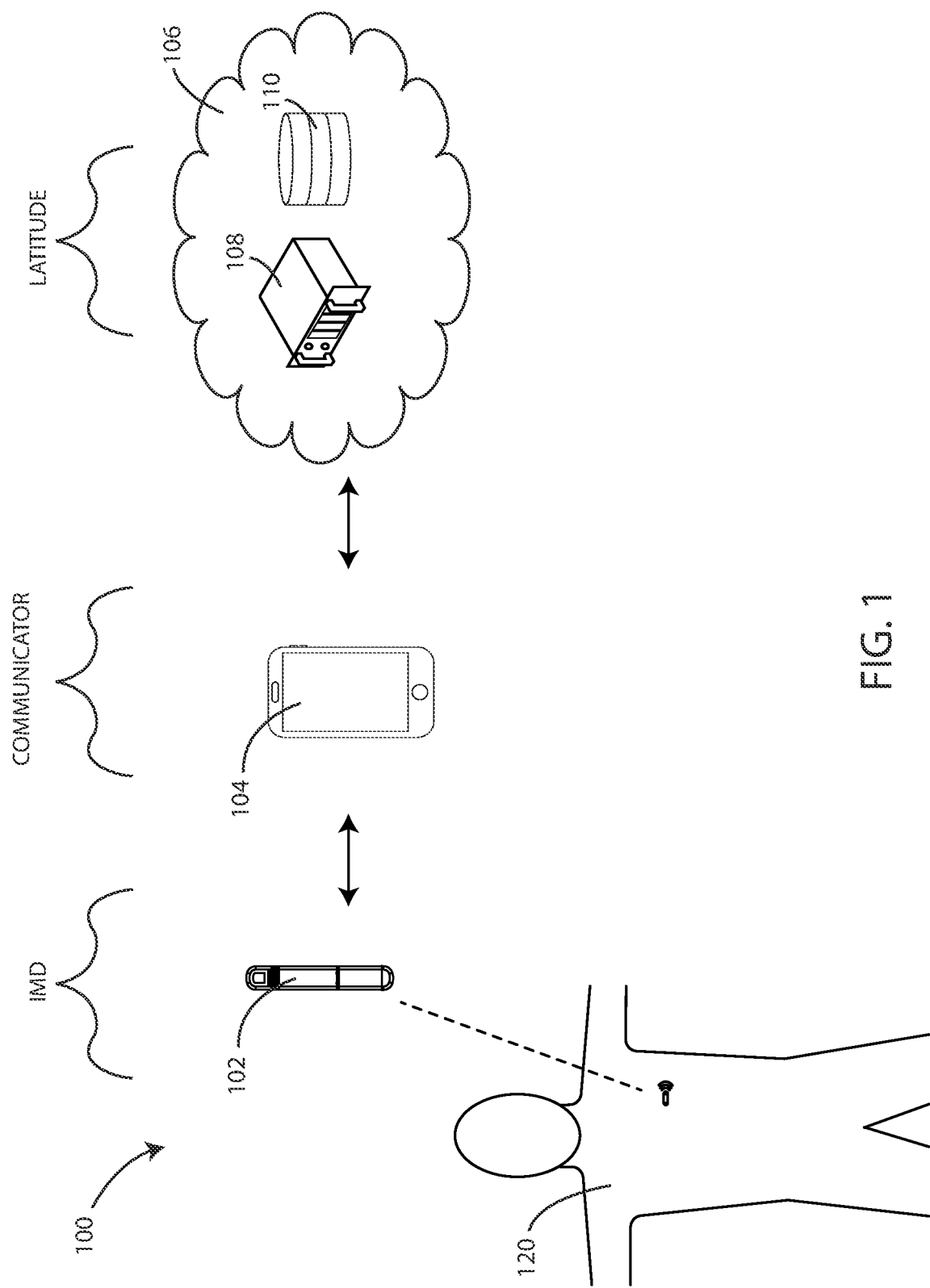
FIG. 1 is a schematic view of components of a system in accordance with various embodiments herein.

Medical data, especially chronic data, can impact the health of a patient and influence physician's decisions. Regulatory bodies are calling for stricter medical data integrity practices. As such, ensuring the authenticity and integrity of the medical device data has become important.

In many cases, an implantable device can be a type of "source device" for patient data and generate substantial amounts of useful patient data. However, many existing implantable devices have memory limitations. Therefore, low device memory typically results in data stored within the implantable device being overwritten. Once data is overwritten, the implantable device (source device) no longer has a record of the data. Therefore, in many cases the authenticity of patient data cannot be verified by simply checking against copies of patient data stored on the implantable device(s).

In accordance with various embodiments herein, blocks of patient data (and in some cases other types of data) from a source device can be processed in order to generate a unique identifier (digest) for that block of data (or file). The function used to create the digest is such that the same unique digest will always be generated for the same block of data or file. Conversely, if the block of data were to change, the output of the function (e.g., the digest) would also change. In this way, the system can verify that the data (such as patient data) has not changed by verifying that the digest has not changed. The function to create the digest can use patient data as well as prior digest data (except in circumstances such as where prior digest data is unavailable) to generate new cumulative digests such that data generated over time is linked together and all prior data can be simultaneously verified by verifying that the most recent digest has not changed. The digest created is very small in comparison to the size of the input block of data or file and can therefore be more easily stored for later use in verification and/or authentication operations.

In some embodiments, digests can be stored and later used to verify or authenticate discrete subunits of large data sets, such as by retaining digests that are specific to subunits of the data sets. For example, in the case of a clinical trial with many patients, many investigators, and many sites, even if some data is corrupted or otherwise comprised, it is valuable to be able to still verify and authenticate the rest of the data that has not been corrupted or otherwise compromised. As such, in various embodiments herein, a discrete subunit of the data set can be excluded, and the rest of the data can still be verified or authenticated.

Digests herein can be generated and/or stored at various logical levels of a system. In some embodiments, digests can be generated and/or stored at the level of an implantable device (as a source device). In some embodiments, digests can be generated and/or stored at the level of an external device in communication with an implantable device. In some embodiments, digests can be generated and/or stored at the level of remote devices (real or virtual) such as devices operating in the cloud and in communication with an implantable device and/or an external device.

When needed, digests stored at various logical levels of the system can be retrieved. For example, a request can be made to one or more source devices in order for them to forward copies of the stored digests they maintain, such as to allow for comparison against digests stored at other logical levels of the system.

However, in some embodiments herein, digests (or digest packets) can be kept on the implantable device and verification operations (such as comparing a digest packet with another) can be executed on the implantable device itself. For example, in some embodiments, digests can be kept on the implantable device and not exported (e.g., the implantable device can be configured to not export the digests that it creates and/or receives). Thus, in some embodiments, the implantable device can receive previously generated data and verify the authenticity of the same by performing a hashing operation on it after receipt and comparing the digest with a digest that was previously generated and stored within the implantable device.

Data verification can be triggered in various ways and at various time points. In some embodiments, data verification can be triggered prior to submission of data to another system, platform or entity. For example, data verification can be triggered before data is transferred from a clinical site to central server or can be triggered before data is transferred to a regulatory agency. In some embodiments, data verification can be triggered at different stages of a clinical trial. In some embodiments, data verification can be triggered periodically or at predefined time points. In some embodiments herein, identification of a data gap for a particular device or patient can trigger a data verification procedure to be performed on other patients such as other patients receiving care at the same clinic, other patients receiving the same type of care, other patients in the same clinical study, etc. For example, if data for a particular device cannot be found and/or authenticated for a particular time period, then that can constitute a data gap and a data verification procedure can be triggered for other patients.

Referring now to FIG. 1, a schematic view of components of a system 100 is shown in accordance with various embodiments herein. The medical device system 100 includes an implantable device 102 and an external device 104. The implantable device 102 can be within a patient 120. FIG. 1 shows a remote location 106. The medical device system 100 also includes a remote server 108 and a remote database 110 at the remote location 106. The remote server 108 and a remote database 110 can be real or virtual. In some embodiments, the remote location 106 can be the cloud.

The implantable device 102 can act as a source device and can gather various pieces of data regarding the patient 120. Examples of patient data are provided in greater detail below. The implantable device 102 can also gather and/or store data regarding the device itself (such as data regarding the programming of the device, changes to the programming, fault conditions, etc.). These types of data can be referred to as "patient device data". In various embodiments, the implantable device 102 can be configured to generate and/or sense patient device data itself. However, in various embodiments, the implantable device 102 can be configured to receive patient device data from external devices, other sensors (implanted or external), input from the patient, and the like.

In various embodiments, the implantable device 102 can be configured to execute one or more operations (such as hashing operations described further below) on units or blocks of patient device data and, in some cases, one or more previous digest packets to create new digest packets. The digest packets can then be used by the system to verify the integrity of the patient data. For example, if the patient device data were to change, then the digest packets created using the same would also change. Thus, verifying that the digest packets have not changed can be used to verify that the patient device data has not changed.

In various embodiments, the implantable device 102 can be configured to forward digest packets onto an external device 104. In various embodiments, the implantable device 102 can be configured to forward only the patient device data and not new digest packets onto an external device 104. In some cases, the external device 104 itself can be used to execute a function to produce digest packets based on the patient device data and/or previous digest packets. For example, in various embodiments, the external device 104 can be configured to receive patient data from the implantable device 102 and execute a hashing operation (described further below) on units of received patient device data and one or more previous digest packets to create new digest packets. In various embodiments, the external device 104 can be configured to store new digest packets. In various embodiments, the external device 104 can be configured to compare digest packets generated with the implantable device 102 against digest packets generated by the external device 104.

In various embodiments, the implantable device 102 can be configured to forward patient device data and/or digest packets onto yet another device other than the external device 104. In various embodiments, the external device 104 can be configured to forward digest packets onto another device of the system when requested to allow patient device data (described further below) to be authenticated.

In various embodiments, the external device 104 can be configured to forward digest packets onto the remote server 108 when requested to allow patient device data (described further below) to be authenticated. In various embodiments, the remote server 108 can be configured to store both patient device data and digest packets in a remote database 110.

In various embodiments, the remote server 108 can be configured to periodically execute a function (such as a hashing operation) on patient device data and previous digest packets and compare the resulting new digest packets against previously received digest packets nominally representing the same patient device data and previous digest packets. In various embodiments, the remote server 108 can be configured to roll back to earlier patient device data and earlier digest packets when the comparison reveals a difference. In various embodiments, the remote server 108 can be configured to digitally sign new digest packets when the comparison reveals no differences. In various embodiments, the remote server 108 can be configured to execute a hashing operation on units of received patient device data and a previous digest packets as received from multiple external devices.

In various embodiments, the remote server 108 can be configured to execute a hashing operation (described further below) on units of received patient device data (described further below) and one or more previous digest packets as received from multiple external devices.

In various embodiments, the remote server 108 can be configured to execute a hashing operation on units of received patient device data and one or more previous digest packets as received from a defined group of external devices. In various embodiments, the remote server 108 can be configured to execute a hashing operation on units of received patient device data and one or more previous digest packets as received from a subset of a group of external devices. In some embodiments, the group of external devices represents all external devices sending patient data as enrolled in a clinical study.

In various embodiments, the implantable device 102 can be configured to overwrite or otherwise discard units of patient device data and/or digest packets periodically, such as to maintain sufficient free space. However, in various embodiments, the implantable device 102 can be configured to discard units of patient data following a different schedule than for discarding digest packets. For example, digest packets can be retained for a longer period of time than patient device data.

The implantable device 102 can include various components as described in more detail below. By way of example, the implantable device 102 include a control circuit, a communication circuit, and one or more sensors. Similarly, the external device 104 can include various components. By way of example, the external device 104 can include a control circuit, and a communication circuit.

Figure 2:
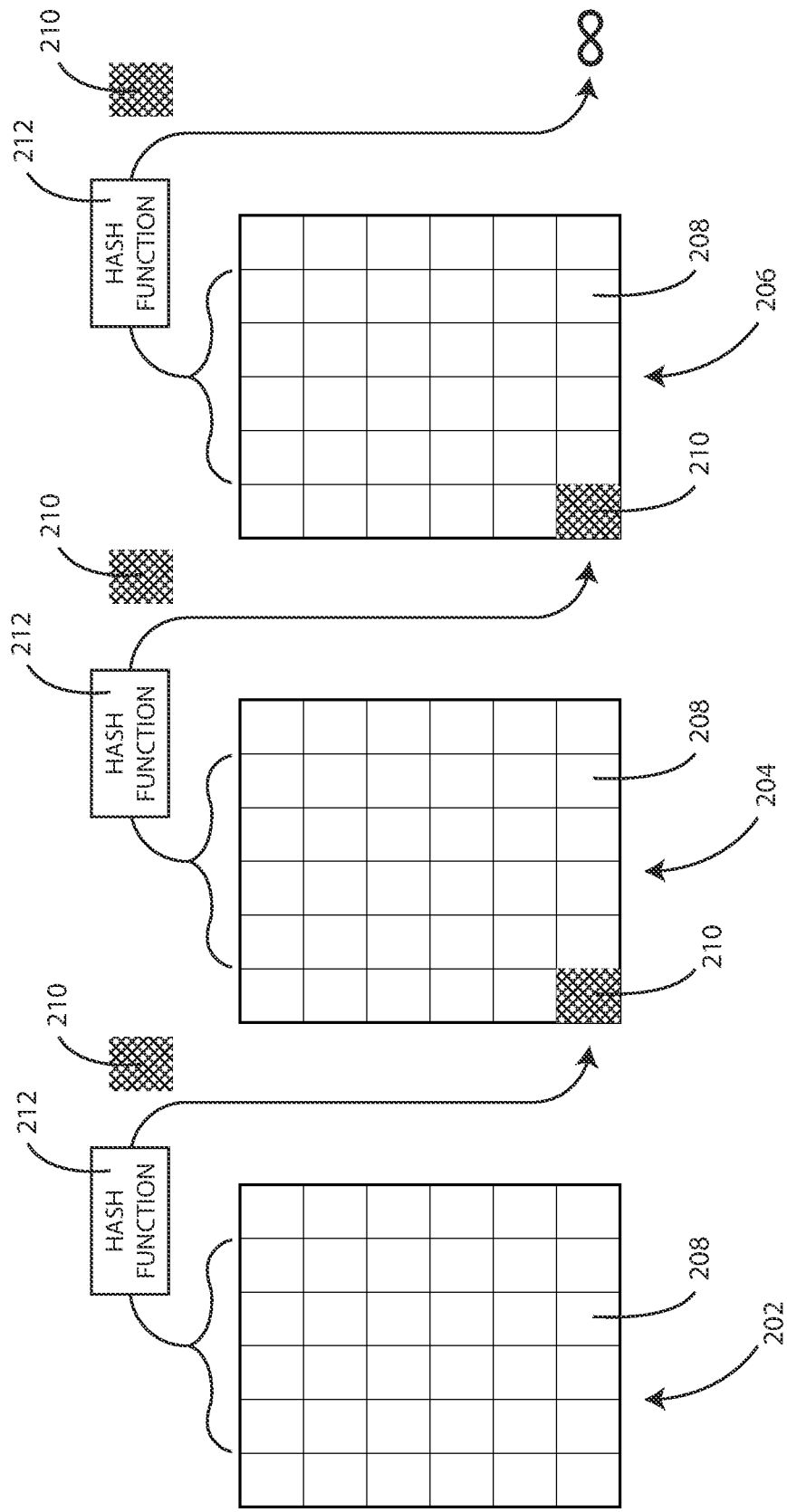
FIG. 2 is a schematic view of operations performed in accordance with various embodiments herein.

Referring now to FIG. 2, a schematic view of operations performed is shown in accordance with various embodiments herein. A medical device system can execute a hashing operation 212 on a first block of data 202 including patient device data 208 in order to create a digest packet 210. Then, the medical device system can execute a hashing operation 212 on a second block of data 204, the second block of data 204 including both new patient device data 208 as well as the previously generated digest packet 210 to create a new digest packet 210. Then, the medical device system can execute a hashing operation 212 on a third block of data 206, the third block of data 206 including both new patient device data 208 as well as the previously generated digest packet 210 to create a new digest packet 210. This cycle can then continue forward continuously ingesting new patient device data and previous digest packets and generating new digest packets.

In some embodiments, the hashing operation 212 can be performed at the level of a source device, such as an implantable medical device. However, in some embodiments the hashing operation 212 can be performed at logical levels of the system that may not themselves generate patient device data. In various embodiments, the hashing operation 212 can be on units of received patient device data 208 and a previous digest packets to create new digest packets. In various embodiments, the hashing operation 212 can be on units of received patient device data 208 and a previous digest packets as received from multiple external devices. In various embodiments, the hashing operation 212 can be on units of received patient device data 208 and a previous digest packets as received from a group of external devices. In various embodiments, the hashing operation 212 can be on units of received patient device data 208 and a previous digest packets as received from a subset of the group of external devices.

It will be appreciated that patient device data and or digest packets can be generated at various logical levels of the system as well as forwarded by and between various logical levels of the system.

Figure 3:
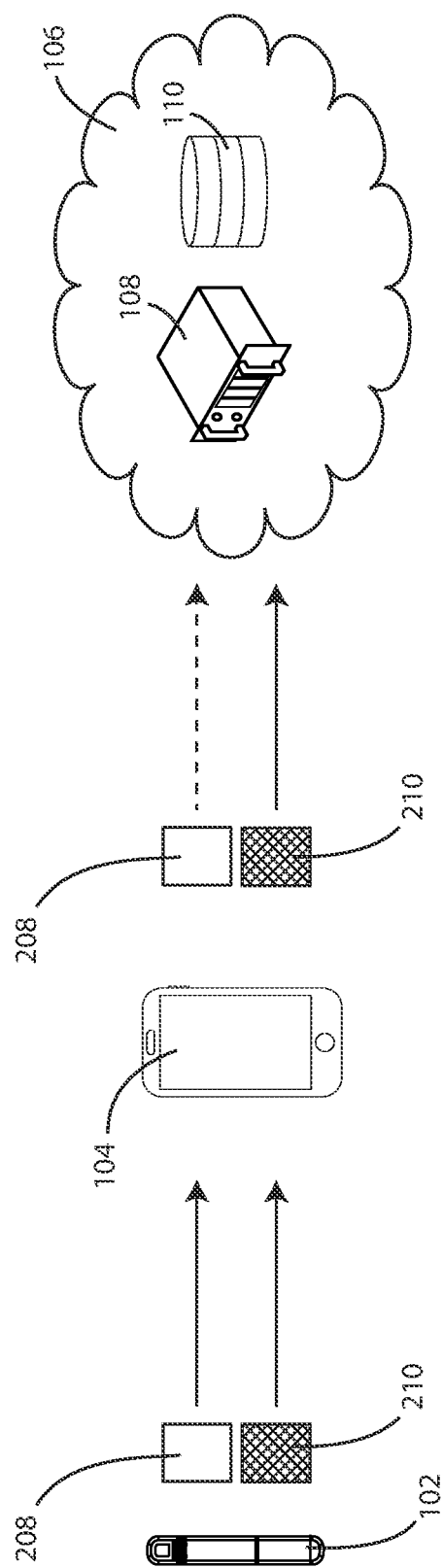
FIG. 3 is a schematic view of components of a system in accordance with various embodiments herein.

Referring now to FIG. 3, a schematic view of components of a system 100 is shown in accordance with various embodiments herein. The medical device system 100 includes an implantable device 102 and an external device 104. The medical device system 100 also includes a remote server 108 and a remote database 110 at a remote location 106.

In this example, the implantable device 102 can serve as a source device and generate patient device data 208. The implantable device 102 can also execute a function in order to create digest packets 210. In this example, the implantable device 102 can forward the patient device data 208 and the digest packets 210 onto the external device 104. In some embodiments, the external device 104 itself can execute a function in order to create digest packets 210. In some embodiments, the external device 104 can compare digest packets it receives with digest packets it creates.

The external device 104 can forward the patient device data 208 and the digest packets 210 onto the remote location 106. Data received at the remote location 106 and/or data generated by the remote server 108 can be stored within the remote database 110. In some embodiments, the remote server 108 itself can execute a function in order to create digest packets 210. In some embodiments, the remote server 108 can compare digest packets it receives with digest packets it creates.

Figure 4:
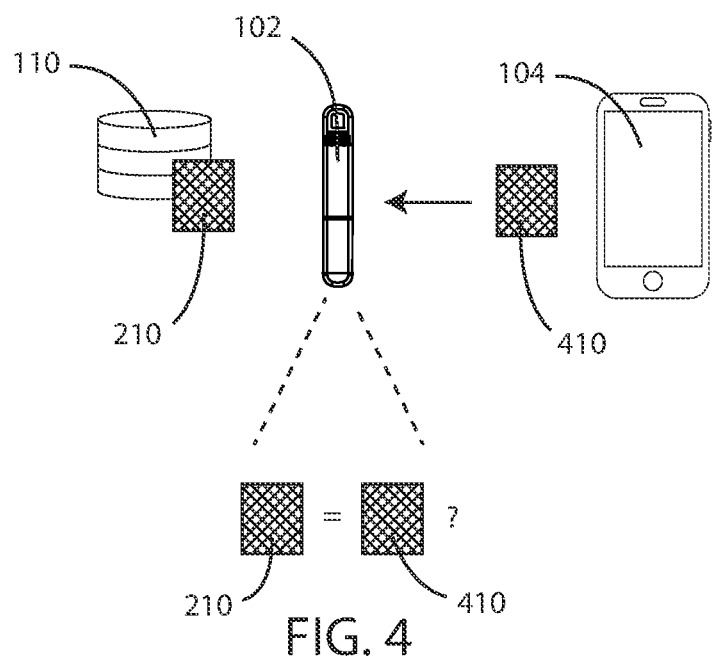
FIG. 4 is a schematic view of components of a system in accordance with various embodiments herein.

For example, referring now to FIG. 4, a schematic view of components of a system 100 is shown in accordance with various embodiments herein. The medical device system 100 includes an implantable device 102. The implantable device 102 includes local storage 410, which can store digest packets 210. The medical device system also includes an external device 104, which can store a separate digest packet 412. The external device 104 can forward one or more separate digest packets 412 to the implantable device 102, which can then compare the stored digest packet(s) 210 with the separate digest packet 412 to ensure they are the same. If not, then the patient device data reflected in the digest packet cannot be verified and/or authenticated and an alert can be generated regarding the same. In some embodiments, the particular implantable device 102 or the particular external device 104 can be flagged as containing patient device data that cannot be verified and/or authenticated.

Figure 5:
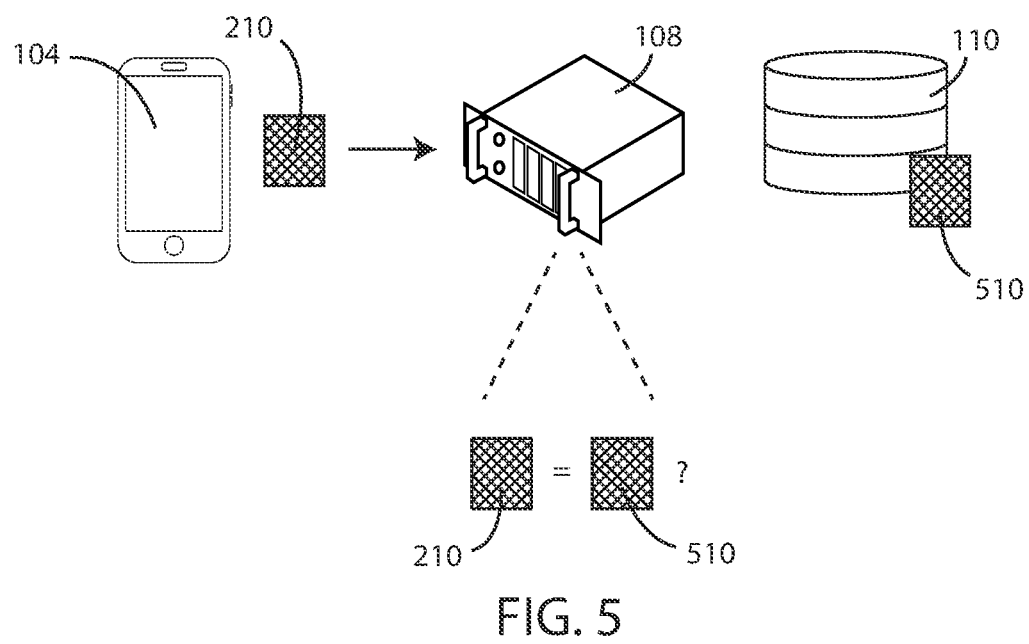
FIG. 5 is a schematic view of components of a system in accordance with various embodiments herein.

Referring now to FIG. 5, a schematic view of components of a system 100 is shown in accordance with various embodiments herein. The medical device system 100 includes an external device 104, a remote server 108, and a remote database 110. The external device can store digest packets 210 (as generated by the external device and/or received from other devices such as an implantable source device). The external device 104 can forward digest packets 210 (and/or patient device data) onto the remote server 108. The remote server 108 can retrieve digest packets 510 (as generated by the remote server 108 and/or received from other devices) and then compare them with the forwarded digest packets 210. If they are not the same, then the patient device data reflected in the digest packet cannot be verified and/or authenticated and an alert can be generated regarding the same. In some embodiments, the particular external device 104 can be flagged as containing patient device data that cannot be verified and/or authenticated.

Data (such as patient device data and/or digest packets) can be forwarded through logical levels of the system taking many different paths. In some embodiments, data that purports to be the same, but has taken different paths to a particular destination can be compared in order to verify and/or authenticate the data.

Figure 6:
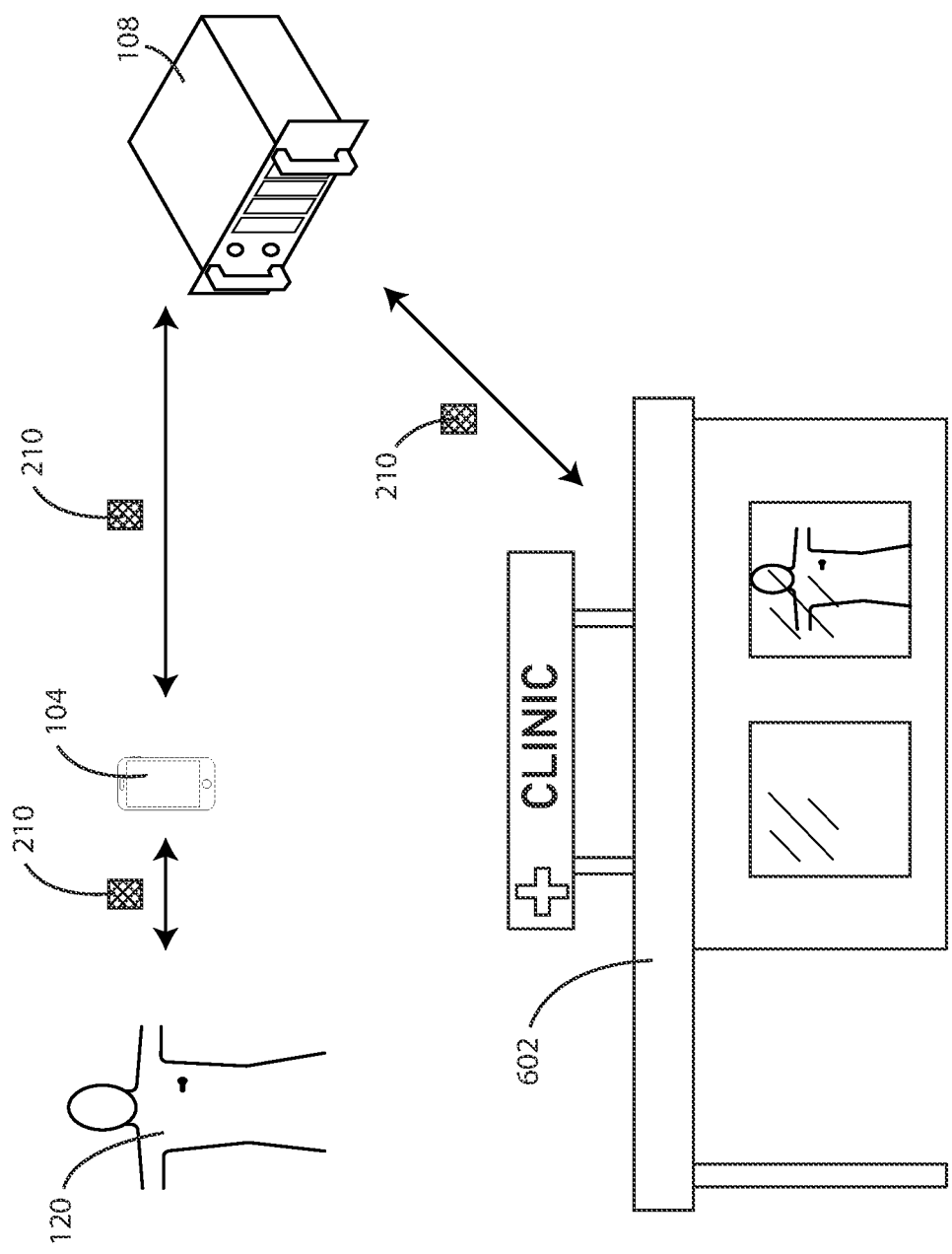
FIG. 6 is a schematic view of components of a system in accordance with various embodiments herein.

Referring now to FIG. 6, a schematic view of components of a system 100 is shown in accordance with various embodiments herein. FIG. 6 shows a patient 120. The patient 120 may have an implantable device (not shown in this view). The medical device system 100 can also include an external device 104. In some embodiments, the external device 104 can receive a digest packet 210 from the implantable device 102 and/or the digest packet 210 can be created at the level of the external device 104. The medical device system 100 can also include a remote server 108. The digest packet 210 from the external device 104 can be forwarded onto the remote server 108.

The patient 120 may also periodically visit a clinic 602 (which may be a typical care visit or could be part of a visit for a clinical study). Equipment at the site of the clinic 602 can also receive digest packets 210 from the implantable device and/or can generate their own digest packets 210 using patient device data. The clinic 602 can forward digest packets 210 (and/or patient device data) onto the remote server 108. The remote server 108 can then compare the digest packets 210 received via the different paths in order to verify and/or authenticate the patient device data reflected by the same.

Patient device data can be used for many different purposes. In some embodiments, patient device data can be used to update therapy parameters and, as such, it is important to be able to verify and/or authenticate the same.

Referring now to FIG. 7, a schematic view of components of a system 100 is shown in accordance with various embodiments herein. The medical device system 100 includes an implantable device 102 in communication with an external device 104. The medical device system also includes a remote server 108 and a remote database 110 at a remote location 106. The external device 104 can be in communication with the remote server 108 and/or the remote database 110 at the remote location 106. In some embodiments, the remote server 108 can authenticate and/or verify patient device data it receives by comparing verification packets. After authentication and/or verification then the remote server 108 can calculate suggested changes to therapy parameters and/or updated therapy parameters. Some exemplary therapy parameters are described below. Such suggested or updated therapy parameters can then be sent back to the implantable device 102 through the external device 104 and/or routed to a clinician for review.

In scenarios where some data is found to be corrupted or otherwise not verifiable, it can be valuable to preserve as much other data as possible. For example, in the context of a clinical study, if data from a particular patient cannot be used, it is valuable if the data from other patients can still be used. As another example, if the data from a particular site (such as a particular clinic) cannot be used, it is valuable if the data from other sites can still be used.

Figure 8:
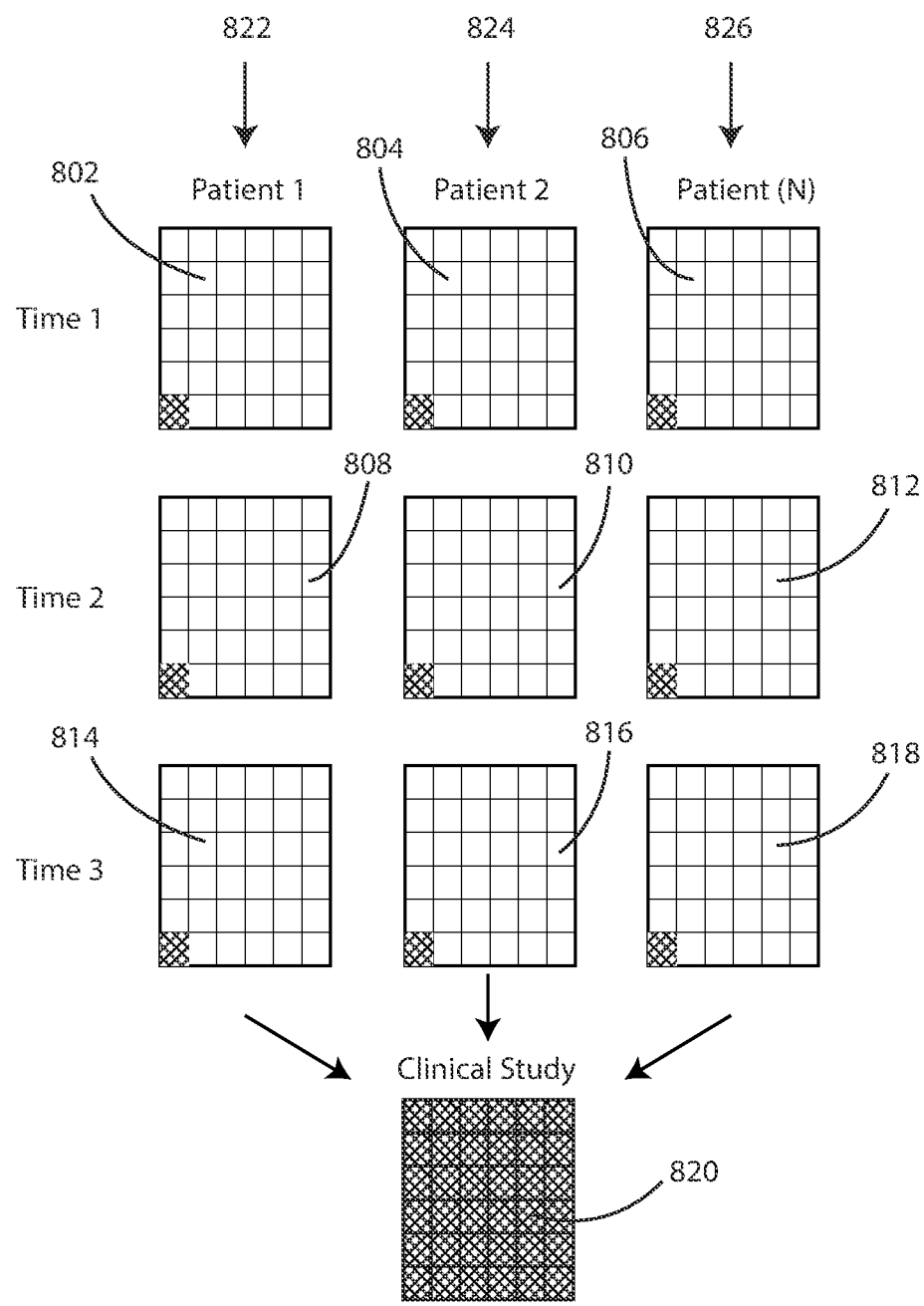
FIG. 8 is a schematic view of data over time in accordance with various embodiments herein.

Referring now to FIG. 8, a schematic view of data over time is shown in accordance with various embodiments herein. FIG. 8 shows patient device data associated with a clinical study 820 over time. In specific, FIG. 8 shows a first patient 822 and patient device data from that first patient from a first time block 802, a second time block 808, and a third time block 814. FIG. 8 also shows a second patient 824 and patient device data from that second patient from a first time block 804, a second time block 810, and a third time block 816. FIG. 8 also shows an "nth" patient 826 and patient device data from that nth patient 826 from a first time block 806, a second time block 812, and a third time block 818. In some embodiments, the data from all of the patients at all of the different times can form data for a clinical study 820. In some embodiments, hash digests for each patient at each time can be maintained as part of the clinical study data along with the underlying patient device data. In this way, if some data is corrupted or changed, only that data representing a particular patient at a particular time need be excluded. However, in other embodiments, hash digests are maintained with less granularity. For example, only a most recent hash digest from a particular patient might be maintained, it being understood that previous hash digests were fed forward along with patient device data to create new hash digests and therefore evaluating only the most recent hash digest for a specific patient is sufficient to verify and/or authenticate all patient device data for that specific patient. There is no particular limit on how the hash digests can be used to group up portions of data for verification and/or authentication. For example, hash digests can be used for all data of a particular patient, all data of a particular site, all data of a particular time, etc.

Figure 9:
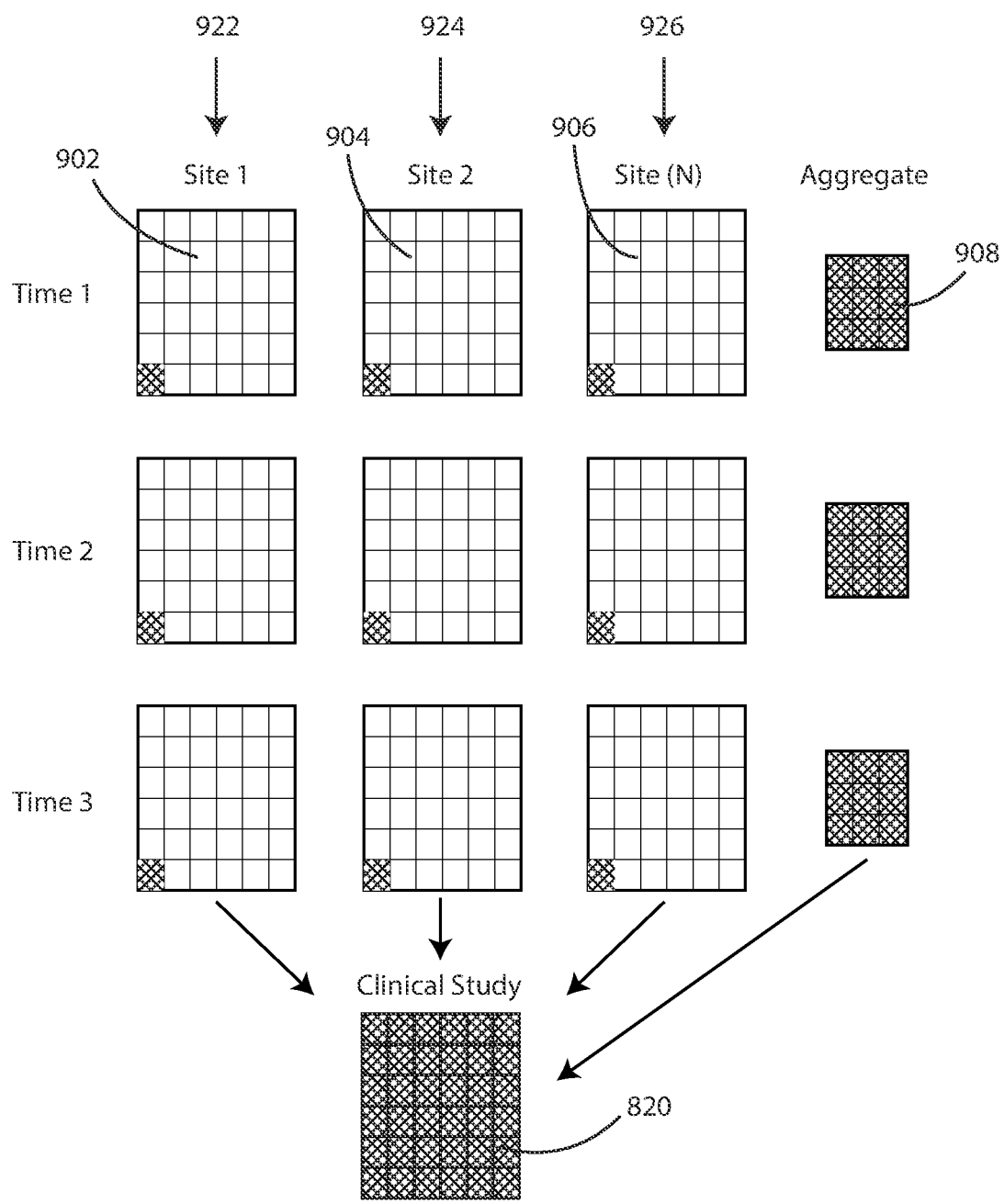
FIG. 9 is a schematic view of data over time in accordance with various embodiments herein.

Referring now to FIG. 9, a schematic view of data over time is shown in accordance with various embodiments herein. FIG. 9 shows patient device data associated with a clinical study 820 over time. In specific, FIG. 9 shows a first site 922 and patient device data from that first site from a first time block 902, a second time block 908, and a third time block 914. FIG. 8 also shows a second site 924 and patient device data from that second site from a first time block 904, a second time block 910, and a third time block 916. FIG. 8 also shows a "nth" site 926 and patient device data from that nth site 926 from a first time block 906, a second time block 912, and a third time block 918. In some embodiments, all patient device data and/or hash digests from a particular time can be rolled into a first time aggregate 928. Similarly, all patient device data and/or hash digests from a later time can be rolled into a second time aggregate 930 and all patient device data and/or hash digests from a still later time can be rolled into a third time aggregate 932.

Figure 10:
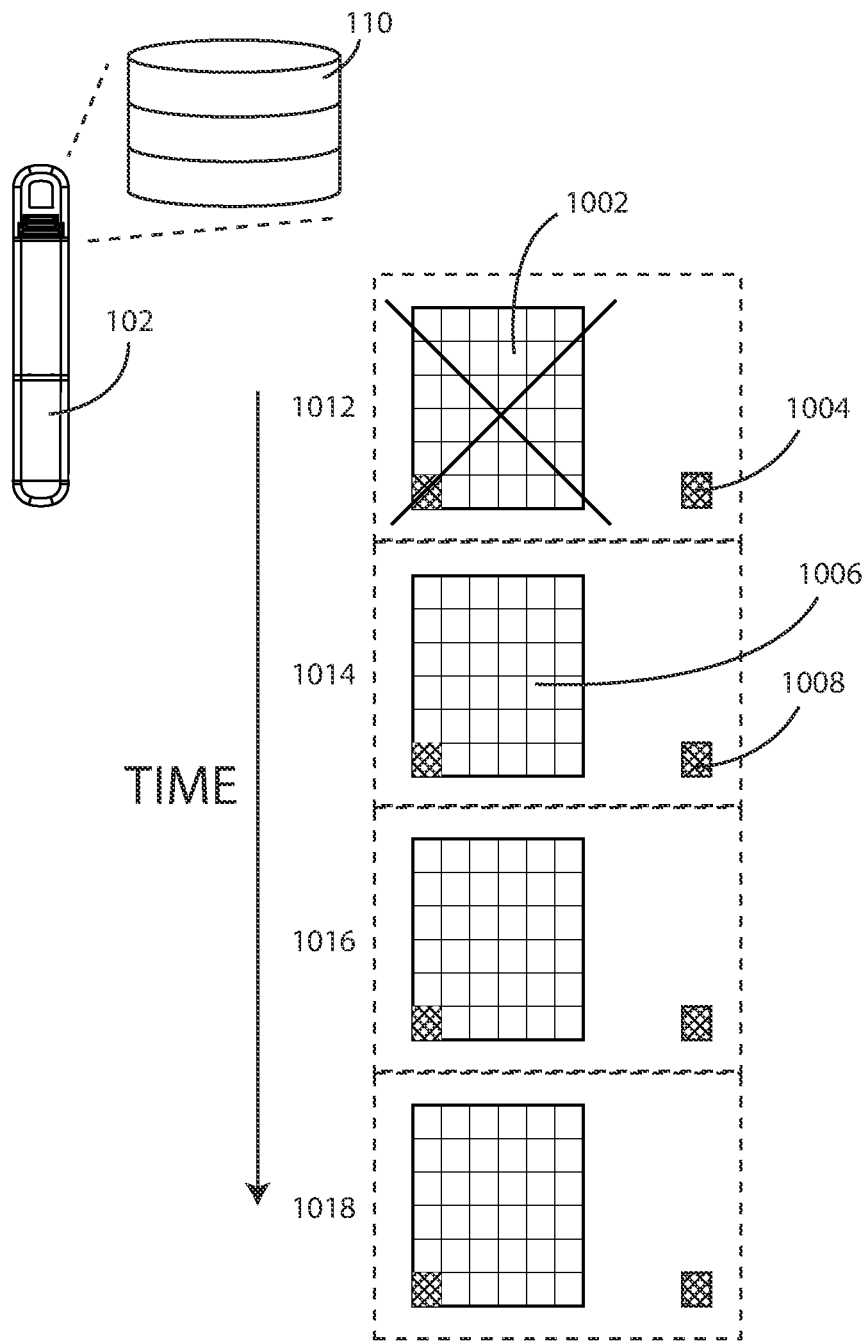
FIG. 10 is a schematic view of components of a system in accordance with various embodiments herein.

Referring now to FIG. 10, a schematic view of components of a system is shown in accordance with various embodiments herein. The system includes an implantable device 102 and local data storage 1010. FIG. 10 shows a first time period 1012. The first time period 1012 includes a first time period data block 1002. The first time period 1012 also includes a first time period digest packet 1004. FIG. 10 also shows a second time period 1014. The second time period 1014 includes a second time period data block 1006. The second time period 1014 also includes a second time period digest block 1008. FIG. 10 shows a third time period 1016 and a fourth time period 1018.

As a result of limited storage in the implantable device 102, the first time period data block 1002 can be overwritten or otherwise discarded while the hash digest 1004 for that time can be retained. At a later time, the second time period data block 1006 may also be overwritten or otherwise discarded while the hash digest 1008 for that time can be retained. As such, to verify and/or authenticate patient device data later, the hash digests can be requested from the implanted device, then hashing can be formed on the patient device data that has been stored away from the implantable device 102 can the two hash digests can be compared. If they are the same, then the patient device data being evaluated can be deemed to be authenticated and/or verified.

Figure 11:
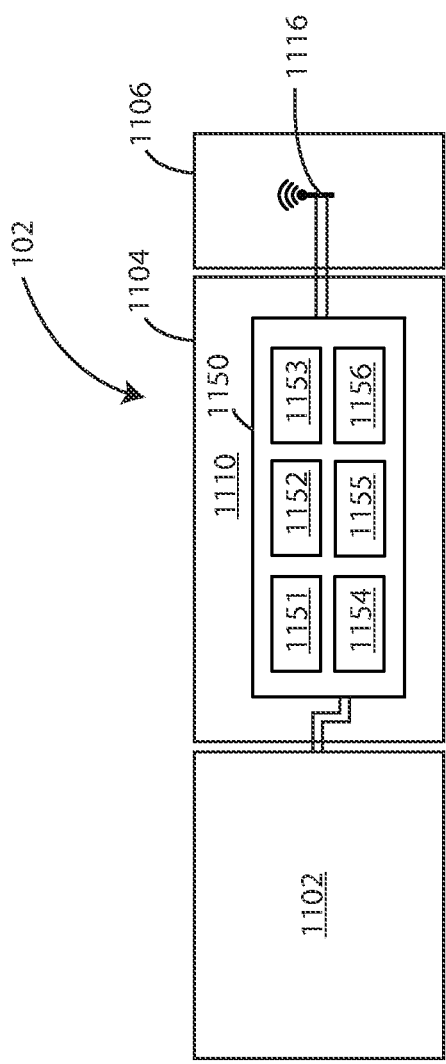
FIG. 11 is a block diagram of components of an implantable medical device in accordance with various embodiments herein.

It will be appreciated that implantable medical devices herein can include many different components depending on the desired functionality. Referring now to FIG. 11 a block diagram is shown of components of an implantable medical device in accordance with various embodiments herein. However, it will be appreciated that various specific embodiments can include a greater number of components, a lesser number of components, or different components.

In this example, the implantable medical device 102 can include a power subunit 1102, an electronics control subunit 1104, and a wireless communications subunit 1106. The power subunit 1102 can include components of an electrochemical cell. The wireless communications subunit 1106 can include an antenna 1116.

In this example, the implantable medical device 102 can include circuitry 1150. The circuitry 1150 can include various electrical components, including, but not limited to a controller 1151 (which can form part of a control circuit), a sensor 1152 (e.g., an accelerometer, a gyroscope, a microphone, a bio-impedance sensor), a microprocessor 1153, therapy unit circuitry 1154, recorder circuitry 1155, and sensor interface circuitry 1156. Other examples of components suitable for use in the medical device systems embodied herein can include telemetry circuitry, memory circuitry (e.g., such as random access memory (RAM) and/or read only memory (ROM)), power supply circuitry (which can include, but not be limited to, one or more batteries, a capacitor, a power interface circuit, etc.), normalization circuitry, control circuitry, electrical field sensor and stimulation circuitry, display circuitry, and the like.

In some embodiments, one or more components can be integrated into the implantable medical device and in other embodiments one or more components can be separate. In some embodiments, recorder circuitry can record the data produced by the sensors of the device and record time stamps regarding the same. In some embodiments, the circuitry can be hardwired to execute various functions while in other embodiments, the circuitry can be implemented as instructions executing on a controller, a microprocessor, other computation device, application specific integrated circuit (ASIC), or the like.

In some embodiments, the implantable medical device 102 can include a chemical sensor. In some embodiments, the chemical sensor is an optical chemical sensor. However, in other embodiments the chemical sensor can be a potentiometric chemical sensor. The chemical sensor can specifically include at least one chemical sensing element, an optical window, and an electro-optical module. The electro-optical module can be in electrical communication with the circuitry within the interior volume 1110. In some embodiments, the chemical sensor can be configured to measure a cellular interstitial component, a blood component, or a breath component, or any analytes thereof. In some embodiments the blood component can include blood constituents or analytes thereof, such as red blood cells; white blood cells including at least neutrophils, eosinophils, and basophils; platelets; hemoglobin; and the like.

The implantable medical device 102 can include a controller 1151. In some embodiments, the controller 1151 can be configured to execute one or more operations described herein. The implantable medical device 102 can include additional components, for example, a therapy unit circuitry 1154. The therapy unit circuitry 1154 can be configured to deliver a therapy to a patient and/or control or influence the delivery of a therapy provided by another device. In some embodiments, the therapy unit can be configured to provide optimum therapy to a patient depending on if they are in a recumbent, standing or sitting position. Examples of therapies can include, but are not limited to, pacing schemes such as rate-adaptive pacing, cardiac-resynchronization therapy (CRT), delivery of a neurostimulation therapy, administration of therapeutic agents, and the like. In some embodiments, the therapy unit circuitry 1154 can be a pharmaceutical therapy unit. In some embodiments, the therapy unit circuitry 1154 can include both an electrical therapy unit and a pharmaceutical therapy unit. In some embodiments, the therapy unit circuitry 1154 can be directed by the controller 1151 to deliver a therapy to a patient.

Figure 12:
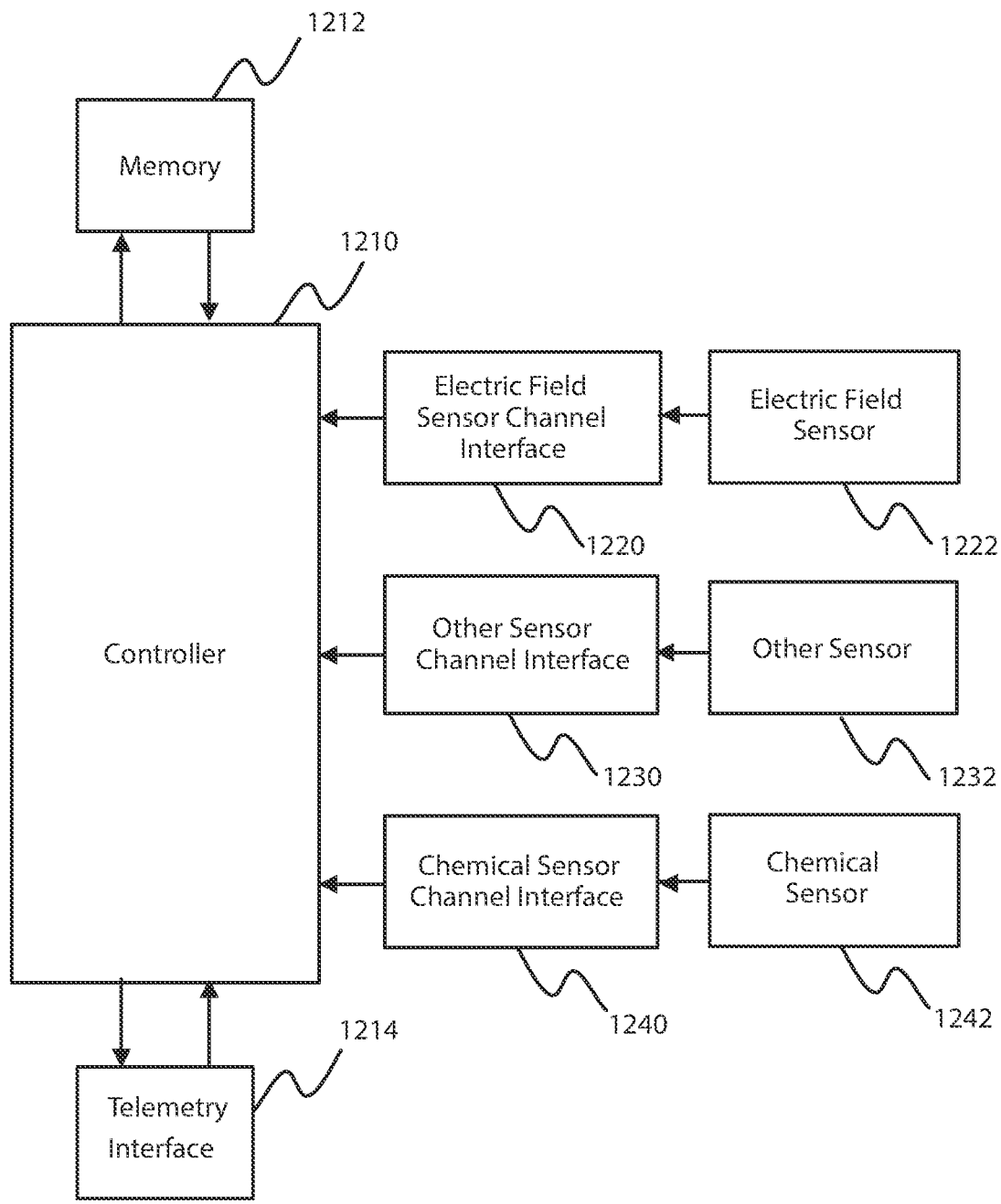
FIG. 12 is a schematic diagram of components of an implantable medical device in accordance with various embodiments herein While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

Referring now to FIG. 12 is a schematic diagram of components of an implantable medical device in accordance with various embodiments herein. Elements of some embodiments of a medical device system are shown in FIG. 12 in accordance with the embodiments herein. However, it will be appreciated that some embodiments can include additional elements beyond those shown in FIG. 12. In addition, some embodiments may lack some elements shown in FIG. 12. The medical device, as embodied herein, can gather information through one or more sensing channels 1220, 1230, 1240. A controller 1210 can communicate with a memory 1212 via a bidirectional data bus. The memory 1212 can include read only memory (ROM) or random-access memory (RAM) for program storage and RAM for data storage.

In some embodiments, a medical device can include one or more electric field sensors 1222 (i.e., electrodes) and an electric field sensor channel interface 1220 that can communicate with a port of controller 1210. The medical device can also include another type of sensor 1232 and a sensor channel interface 1230 for the same that can communicate with a port of controller 1210. The medical device can also include one or more chemical sensors 1242 and a chemical sensor channel interface 1240 that can communicate with a port of controller 1210. The channel interfaces 1220, 1230 and 1240 can include various components such as analog-to-digital converters for digitizing signal inputs, sensing amplifiers, registers that can be written to by the control circuitry to adjust the gain and threshold values for the sensing amplifiers, and the like. A telemetry interface 1214 is also provided for communicating with external devices such as a programmer, a home-based unit, and/or a mobile unit (e.g. a cellular phone, laptop computer, etc.).

In some embodiments, the medical device can also include additional sensors, such as posture sensors, activity sensors, or respiration sensors integral to the medical device. In some embodiments, the medical device can also include additional sensors that are separate from medical device. In various embodiments one or more of the posture sensors, activity sensors, or respiration sensors can be within another implantable medical device communicatively coupled to the medical device via telemetry interface 1214. In various embodiments one or more of the additional posture sensors, activity sensors, or respiration sensors can be external to the body and are coupled to medical device via telemetry interface 1214.

In some embodiments herein, a plurality of devices (such as all devices representing a certain set of patients, a certain set of devices, etc.) can be pinged with a request for them to transmit their identity and their most recent hash. In some embodiments, the most recent hash that is requested and transmitted back to the requestor can serve as verification of the device identity as well as verification of the patient identity (such as in the case of an implantable device that is permanently implanted in a particular patient). In some embodiments, data regarding the identity of the device can be included as part of the data that is hashed and therefore the hash can be unique to a given device and thus different than if the same underlying clinical data were hashed by another device.

Methods

Many different methods are contemplated herein, including, but not limited to, methods of tracking patient device data, verifying patient device data, authenticating patient device data, methods of using patient device data, methods of tracking clinical study data, and the like. Aspects of system/device operation described elsewhere herein can be performed as operations of one or more methods in accordance with various embodiments herein.

In various embodiments, a method herein can include generating patient device data and/or receiving patient device data from the implantable device. A method can further include executing a hashing operation on units of generated and/or received patient device data and one or more previous digest packets to create new digest packets. In some embodiments, a method can include storing new digest packets and/or forwarding digest packets onto another device of the system when requested to allow patient data to be authenticated.

In various embodiments, a method herein can include at least one of the implantable device, an external device, a separate device, and/or a remote server executing a hashing operation on units of patient data and one or more previous digest packets to create new digest packets.

In various embodiments, a method can include, at least one of the implantable device, an external device, a separate device, and/or a remote server forwarding digest packets onto another device.

In various embodiments, a method herein can include at least one of the implantable device, an external device, a separate device, and/or a remote server comparing digest packets generated against digest packets generated by another device.

In various embodiments, a method herein can include at least one of the implantable device, an external device, a separate device, and/or a remote server storing both patient data and digest packets in data storage and/or a database.

In various embodiments, a method herein can include at least one of the implantable device, an external device, a separate device, and/or a remote server periodically rehashing patient data and previous digest packets and comparing the resulting new digest packets against previously received digest packets nominally representing the same patient data and previous digest packets. In various embodiments, at least one of the implantable device, an external device, a separate device, and/or a remote server can roll back to earlier patient data and earlier digest packets when the comparison reveals a difference. In various embodiments, at least one of at least one of the implantable device, an external device, a separate device, and/or a remote server can digitally sign the resulting new digest packets when a comparison reveals no differences.

In various embodiments, a method herein can include at least one of the implantable device, an external device, a separate device, and/or a remote server executing a hashing operation on units of received patient device data and one or more previous digest packets as received from multiple external devices.

In various embodiments, a method herein can include at least one of the implantable device, an external device, a separate device, and/or a remote server executing a hashing operation on units of received patient device data and one or more previous digest packets as received from a group of external devices, and executing a hashing operation on units of received patient device data and one or more previous digest packets as received from a subset of the group of external devices.

Hashing Operations

Various embodiments herein include execution of a hashing operation. Further details about exemplary hashing operations are provided as follows. However, it will be appreciated that this is merely provided by way of example and that further variations are contemplated herein. As used herein, hashing operations shall also include checksum functions and cyclic redundancy check functions, unless the context dictates otherwise.

In various embodiments, a device of a system herein (such as an implantable device, an external device, a remote device such as a remote server, and the like) is configured to execute a hashing operation on units of patient data. In various embodiments, a device of a system herein is configured to execute a hashing operation on units of patient data and one or more previous digest packets to create new digest packets.

Various methods of hashing can be used herein. Hashing functions can specifically include universal hash functions, non-cryptographic hash functions, keyed cryptographic hash functions, unkeyed cryptographic hash functions, and the like. Exemplary hash functions can include, but are not limited to, BLAKE-256, BLAKE-512, BLAKE2s, BLAKE2b, BLAKE2X, BLAKE3, ECOH, FSB, GOST, Grøstl, HAS-160, HAVAL, JH, LSH[12], MD2, MD4, MD5, MD6, RadioGatún, RIPEMD, RIPEMD-128, RIPEMD-160, RIPEMD-320, SHA-1, SHA-224, SHA-256, SHA-384, SHA-512, SHA-3 (subset of Keccak), Skein, Snefru, Spectral Hash, Streebog, SWIFFT, Tiger, and Whirlpool.

Execution of hashing operations herein can take place at various time points and/or in response to detection of various events. In some embodiments, hashing operations can be executed when a threshold amount of data (such as patient device data) has been reached. In some embodiments, hashing operations can be executed when an event occurs that represents a risk of data loss. For example, if a time-varying magnetic field such as that associated with an MRI machine is detected, then hashing operations could be executed. In some embodiments, hashing operations can be executed when a clinically relevant time point occurs. For example, in some embodiments, hashing operations can be executed when the patient visits a clinic (which can be determined based on geolocation data or detection of interrogation of the device). In some embodiments, hashing operations can be executed when the implantable device receives new programming via an external device (e.g., the implantable device received new parameters for therapy).

Patient Device Data

Various embodiments herein include and/or operate on patient device data. Further details about the patient data are provided as follows. However, it will be appreciated that this is merely provided by way of example and that further variations are contemplated herein.

Patient device data can include, but is not limited to, physiological data, heart rate data, heart rate variability data, electrogram data, blood pressure data, heart rhythm episode data, heart sounds data, decompensation data, temperature data, sympathetic nervous data, optical sensor data, blood glucose values, pulse oximetry data, physiological analyte values (such as electrolyte levels, biomarker levels, and the like), respiration rate, tidal volume, detected events, detected coughing, detected syncope, other diagnostics data, other cardiopulmonary data, other implanted sensor data, device data such as device programming parameters, records of therapy administered, battery level data, records of communications with other devices, interrogation data, and the like. Programming parameters can include, but are not limited to, lower rate limit, right ventricular pacing threshold, left ventricular pacing threshold, dynamic atrioventricular delay response factor, paced atrioventricular delay, interventricular delay, and ventricular rate regulation. Atrioventricular (A/V) delay can be RA-RV delay, RA-LV delay, and LA-LV delay, as examples.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device system comprising:
   an implantable device comprising
      an implantable device control circuit;
      an implantable device communication circuit in electrical communication with the implantable device control circuit; and
      one or more sensors configured to sense patient data;
   an external device comprising
      an external device control circuit; and
      an external device communication circuit in electrical communication with the external device control circuit;
   wherein the external device communication circuit is configured to receive the patient data from the implantable device communication circuit and receive one or more previous digest packets, and wherein the external device control circuit is configured to execute a hashing operation on units of the patient data received from the implantable device communication circuit and the one or more previous digest packets to create new digest packets;
   wherein the external device is configured to store the new digest packets;
   wherein the external device is configured to forward the new digest packets onto another device of the medical device system to allow the patient data to be authenticated.

2. The medical device system of claim 1, the medical device system further comprising a remote server and a remote database, wherein the remote server serves as the another device of the medical device system.

3. The medical device system of claim 1, wherein the implantable device is configured to execute a hashing operation on the units of the patient data and the one or more previous digest packets to create a new device set of digest packets.

4. The medical device system of claim 3, wherein the implantable device is configured to forward the new device set of digest packets onto the external device.

5. The medical device system of claim 4, wherein the external device is configured to compare the new device set of digest packets generated with the implantable device against the new digest packets generated by the external device.

6. The medical device system of claim 2, wherein the remote server is configured to store the patient data and the previous digest packets, and the new digest packets in the remote database.

7. The medical device system of claim 6, wherein the remote server is configured to periodically rehash the patient data and the previous digest packets to create new remote server digest packets and compare the new remote server digest packets against the new digest packets, nominally representing the patient data and the previous digest packets.

8. The medical device system of claim 7, wherein the remote server is configured to store earlier patient data and earlier digest packets in the remote database and to roll back to the earlier patient data and the earlier digest packets when the comparison reveals a difference.

9. The medical device system of claim 7, wherein the remote server is configured to digitally sign the resulting new digest packets when the comparison reveals no differences.

10. The medical device system of claim 6, wherein the remote server is configured to
   execute a hashing operation on the units of the patient data and one or more previous external device digest packets as received from a group of external devices; and
   separately execute a hashing operation on the units of the received patient device data and one or more previous subset external device digest packets as received from a subset of the group of external devices.

11. The medical device system of claim 10, wherein the subset of the group of external devices represents external devices from a particular site in a clinical study.

12. The medical device system of claim 2, wherein the remote server is configured to send a request to a plurality of implantable devices requesting them to transmit their identity and their most recent digest packets.

13. The medical device system of claim 1, wherein the external device is configured to detect an event and executes the hashing operation in response to the detected event.

* * * * *